United States Patent [19]

Karlsson

[11] 4,041,379

[45] Aug. 9, 1977

[54] APPARATUS FOR TESTING METAL BLANKS UTILIZING AT LEAST ONE INSPECTING HEAD MOVED ALONG THE SURFACE THEREOF

[75] Inventor: Per-Olle Karlsson, Oxelosund, Sweden

[73] Assignee: Granges Oxelosunds Jarnverk AB, Sweden

[21] Appl. No.: 591,938

[22] Filed: June 30, 1975

[30] Foreign Application Priority Data

Aug. 19, 1974 Germany .............................. 2439662

[51] Int. Cl.² ........................................... G01R 33/12
[52] U.S. Cl. .................................... 324/37; 73/67.8 S
[58] Field of Search ................. 324/37, 40; 73/67.8 S, 73/71.5 US; 33/1 M, 174 L, 174 P, 174 PA

[56] References Cited

U.S. PATENT DOCUMENTS

| 3,234,457 | 2/1966 | Sower et al. | 324/40 |
| 3,447,074 | 5/1969 | Sower et al. | 324/37 |
| 3,460,028 | 8/1969 | Beaver et al. | 324/37 |
| 3,899,734 | 8/1975 | Beaver et al. | 324/37 |

OTHER PUBLICATIONS

Nakaoka et al.; Billet Automatic Inspection Machine; Shimadzu Rev. (Japan); vol. 28, No. 4 (1971); pp. 17–22.

*Primary Examiner*—Robert J. Corcoran
*Attorney, Agent, or Firm*—Craig & Antonelli

[57] ABSTRACT

Apparatus for non-destructive testing of metal blanks, in particular steel slabs, flat steel, billets or blooms, for defects such as cracks, seams, cavities, bubbles or the like disposed at or near the surface comprising one or more inspecting heads movable relatively to the surface of the test objects and provided with inspecting means for detecting such defects, said inspecting heads being held by means of pressure and tension members which are carried by a common support arm and transmit the pressure and tension forces substantially separately from each other so as to be individually movable up and down perpendicularly to the slab surface and constrained to move in the travelling direction in engagement with the slab surface.

22 Claims, 6 Drawing Figures

APPARATUS FOR TESTING METAL BLANKS UTILIZING AT LEAST ONE INSPECTING HEAD MOVED ALONG THE SURFACE THEREOF

The invention relates to an apparatus for non-destructive testing of metal blanks, in particular steel slabs, flat steel, billets or blooms for defects such as cracks, seams, cavities, bubbles or the like, disposed at or near the surface comprising inspecting means movable relatively to the surface of the test objects and detecting such defects.

The possibility of detecting all these defects in the slab stage are very unreliable and are usually conducted visually. Test methods have also been proposed which detect the defects in their position and in their depth path, i.e., three dimensionally, more especially by means of eddy current or leakage flux measuring techniques in which the magnetic stray field is sensed and measured either by means of probe-like inspecting members, such as surface-wave probes, magnet-sensitive semiconductors, induction coils or the like, preferably in differential circuit connection. A difficulty with such testing methods resides in that the result is falsified by fluctuations of the distance between the slab surface and the inspecting means, such fluctuations being caused by the in some cases considerable surface irregularities of the test objects, in particular the steel slabs.

The problem underlying the present invention is to obviate this disadvantage and provide an apparatus which makes it possible for the inspecting means during the scanning of the slab surface to remain constantly in engagement with the slab surface irrespective of surface irregularities and to be moved exactly in the sensing direction over the slab surface without lateral displacement or yielding. According to the invention this problem is solved in that by means of pressure and tension members which are carried by a common support arm and transmit the pressure and tension forces substantially separately from each other one or more inspecting heads provided with inspecting means are held so as to be individually movable up and down perpendicularly to the slab surface and constrained to move in the travelling direction in engagement with the slab surface.

The apparatus according to the invention affords the advantage of a substantially exact detection of the location and depth of the defects. It has been found that the defect depth path can be detected by the apparatus according to the invention to within ± 0.5 to 1 mm. This substantially exact detection of the defect depth has the advantage that when these defects are machined out there is no unnecessary loss of material due to machining the steel slab too deeply.

According to the invention it is advantageous if each inspecting head is tiltable at least about one tilt axis extending substantially transversely of the travelling direction and substantially parallel to the slab surface so that each inspecting head can at least adapt itself to the surface waves in the travelling direction. It has been found particularly advantageous in each inspecting head is tiltable about a second tilt axis extending substantially parallel to the travelling direction and substantially parallel to the slab surface. The inspecting head can thereby adapt itself substantially to all the irregularities of the slab surface and slide over said surface in constant engagement.

According to the invention each inspecting head is engaged by a pressure member of variable length which is mounted with its one end of the support arm and with its other end on the inspecting head, the pressure members pressing the inspecting heads with a predetermined pressure against the slab surface.

It is advantageous to use as pressure members double acting pneumatic or hydraulic cylinders, with the aid of which each inspecting head can be raised from the slab surface after the inspecting operation.

According to the invention each inspecting head is engaged by at least one tension member which is connected with its one end to the support arm and with its other end to the lower region of the inspecting head, the tension members extending substantially horizontally and being pivotal at least about a tilt axis extending substantially parallel to the slab surface and transversely of the travelling direction.

To increase the directional stability of the inspecting heads in the desired travelling direction it has been found particularly advantageous to employ two crossed tension members. These are advantageously connected in each case to the support arm and the inspecting head by means of ball head joints. A pivoting of the tension members is thus possible about an axis extending perpendicularly to the travelling direction and parallel to the slab surface with simultaneous mutual twisting of the tension members which is produced by a tilting of the inspecting head about the axis extending parallel to the travelling direction.

To avoid mutual obstruction of the tension members, in the region of the intersection according to the invention at least one of the tension members comprises a U-shaped curved portion which extends round the other tension member.

According to the invention it is advantageous to use as tension members drawbar-like tie members which consist of at least two components rotatable with respect to each other about the longitudinal axis of the tie member, the arranement being such that the effective length of the tie members remains substantially constant on rotation of the components.

According to the invention a constrained guiding of the inspecting heads in the desired travelling direction may be achieved in that the pressure members are mounted on the support arm via a swivel joint whose pivot axis extends perpendicularly to the travelling direction of the inspecting heads and parallel to the slab surface.

The tilting movements of the inspecting heads about the tilt axes extending perpendicularly to the travelling direction and parallel to the slab surface and about the axis extending parallel to the travelling direction are advantageously effected in that the other end of the pressure members facing the inspecting heads is connected to the associated inspecting head via a universal joint.

According to the invention the constrained guiding of the inspecting head in the desired travelling direction is also effected in that the tension members are crossed and at their intersections are connected by a connecting pin led through both tie members in such a manner that inspite of the twisting of the tie members about the axis extending parallel to the travelling direction no lateral displacement of the inspecting heads from the path of movement is possible.

It is advantageous to lead the connecting pin through the tension members perpendicularly to the plane formed by said tension members in the untwisted position, said pin being fixedly arranged in the one tension member and in the other displaceable in the direction of its axis. This prevents any alteration of the angle formed by the crossed tension members even with mutual twisting of said members.

According to the invention the inspecting heads are individually mounted on the support arm in a line adjacent each other, the spacing between adjacent inspecting heads being substantially equal to the sensing width defined by the inspecting means disposed in the head or to an integral multiple thereof. The support arm with the inspecting heads is displaced by 1, 2, 3 etc., sensing widths perpendicularly to the sensing strips defined by the inspecting means and the slab surface then scanned in the same manner until said surface has been substantially completely scanned.

It has been found advantageous for the support arm for the inspecting heads to extend perpendicularly to the movement direction substantially over the entire surface area to be scanned. Since the thickness of the slabs depends on the nature of their production and the dimensions of the metal sheets to be rolled can be between 100 and about 600 mm, the suport arm 3 is adjustable by means of a coarse adjusting device by about 500 to 600 mm perpendicularly to the support surface of the slabs, the distance of the lower edge of the support arm to the slab surface to be inspected preferably being set to about 50 to 60 mm by means of said coarse adjusting device.

Preferably, the length of the support arm is made equal only to a fraction of the maximum possible extent of the surface area to be inspected in the direction of the support arm and after the complete scanning of a support arm width of the slab surface the support arm with the inspecting heads is displaced substantially by the support arm length in the direction of the support arm to scan the adjacent slab surface area in the same manner as the first area.

According to the invention the tension and pressure members are so dimensioned that the inspecting heads are movable out of their normal position at least up to about 30 to 50 mm upwardly and at least up to about 40 to 60 mm downwardly without substantially changing the bearing pressure and the apparatus according to the invention is thus suitable for test objects such as slabs, flat steel, billets or blooms whose thickness varies by about 70 to 110 mm.

It has been found particularly advantageous for the contact surface of the inspecting heads to consist of a substantially highly wear-resistant sliding material.

According to the invention each inspecting head comprises inspecting means which are fixedly arranged within the heads in the region of the inner side of the contact surface and/or reciprocal at a fixed distance from the contact surface. Particularly suitable as inspecting means are probes connected in differential circuit arrangements and measuring a magnetic stray field, such as surface-wave probes, magnet-sensitive semiconductors, induction coils or the like, or eddy current probes connected in differential circuit.

Since the weight of the inspecting heads themselves and the resultant bearing pressure of the inspecting heads on the slab surface can be very large, to reduce sliding friction it may be advantageous to influence the pressure members constructed as piston and cylinder units in the stroke direction so that part of the weight of the inspecting heads is compensated and the heads are held with a predetermined pressure in engagement with the slab surface, said pressure being less that the weight of the inspecting heads.

The invention will be explained in detail hereinafter with the aid of the schematic drawings of examples of embodiment.

Figure 1:
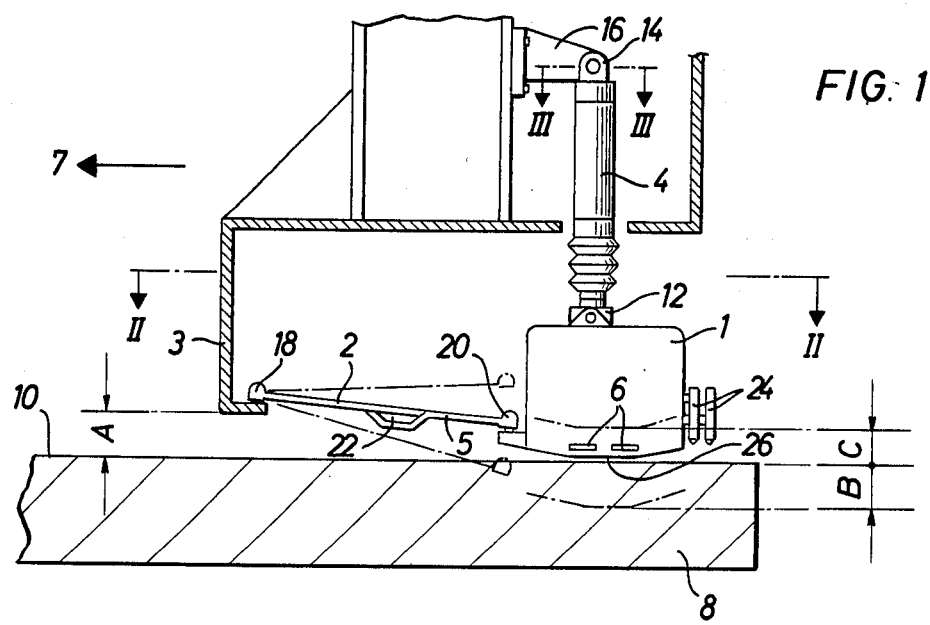
FIG. 1 is a side view of part of an apparatus according to the invention, partially in section.
Figure 2:
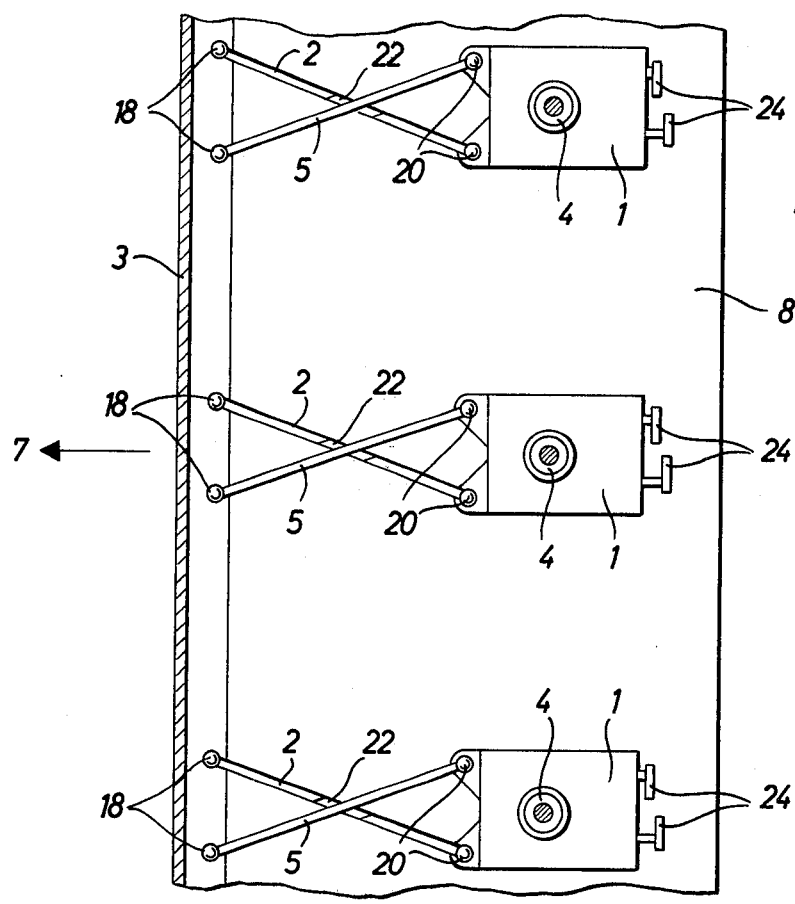
FIG. 2 is a section along the line II—II of FIG. 1 seen from above.

In the example of embodiment according to FIGS. 1 and 2 the inspecting heads provided with inspecting means 6 are held by means of a pressure member 4 and tension members 2 and 5 mounted on a common support arm and transmitting the pressure and tension forces substantially separately so that said heads are movable individually up and down and in a line at a predetermined spacing adjacent each other perpendicularly to the slab surface 10, are constrained to move in the travelling direction 7 and in engagement with the slab surface 10.

Each inspecting head 1 is engaged by a pressure member 4 of variable length, said member being mounted with its one end on a holder 16 of the support arm 3 ad with its other end on the inspecting head 1 and each head is pressed with a predetermined force against the slab surface. The pressure member 4 is preferably constructed as a double acting pneumatic or hydraulic cylinder.

The tension forces to be exerted by the support arm 3 on the inspecting heads 1 are transmitted substantially by the tension members 2 and 5 which are each connected with their one end to the support arm 3 and with their other end to the lower region of the inspecting head 1, the tension members extending substantially horizontally. The tension members 2 and 5 are crossed to increase the directional stability of the inspecting heads 1 in the desired travelling direction. At their ends the tension members 2 and 5 each comprise ball head joints 18 and 20 via which they are connected to the support arm 3 and the inspecting head 1. This arrangement and mounting of the tension members 2 and 5 permits a pivoting of said members about an axis extending substantially parallel to the slab surface 10 and transversely of the travelling direction 7 with simultaneous mutual twisting which is produced by a tilting of the inspecting head 1 about an axis extending parallel to the travelling direction 7.

To avoid mutual obstruction of the tension members 2 and 5 the lower member 5 comprises in the region of the intersection a U-shaped curve portion 22 which extends round the other rectilinearly extending tension member 2.

By means of a universal joint 12 mounted at the top in the region vertically above the contact surface 26 of the inspecting head 1, substantially centrally within said region, the inspecting head is connected to the pressure member 4 in such a manner that it is tiltable both about a first tilt axis extending transversely of the travelling direction 7 and parallel to the slab surface 10 and about a second tilt axis extending parallel to the travelling direction 7. Consequently, the inspecting head 1 can be held constantly in engagement with the slab surface 10 in spite of irregularities in said surface.

The constrained guiding of the inspecting heads 1 in the desired travelling direction 7 is effected in that the pressure member 4 is mounted via a swivel joint 14 on the holder 16 of the support arm 3, the pivot axis thereof extending perpendicularly to the travelling direction 7 of the inspecting heads 1 and parallel to the slab surface 10.

The inspecting heads are mounted in a line adjacent each other on the support arm 3 individually so that the distance between adjacent heads 1 is substantially equal to twice the scanning width defined by the inspecting means 6 disposed in the head 1.

The support arm 3 for the inspecting heads 1 extends perpendicularly to the travelling direction 7 substantially over the entire surface area to be scanned. Since the thickness of the slabs 8 depending upon the nature of their production and the thickness of the metal sheets to be rolled therefrom can vary by about 100 to 600 mm the support arm 3 is arranged to be adjustable perpendicularly to the support surface of the slab 10 through about 500 to 600 mm by means of a coarse setting device which is not illustrated and the distance A of the lower edge of the support arm 3 to the slab surface 10 is preferably about 50 to 60 mm. As coarse adjusting device a double acting hydraulic cylinder or an adjustment spindle is preferably used.

The tension and pressure members 2, 5 and 4 are so dimensioned that the inspecting heads 1 are movable out of their normal position at least up to about 30 to 50 mm upwardly and at least up to about 40 to 60 mm downwardly without substantially changing the contact pressure and consequently the apparatus according to the invention can be used for slabs, flat steel, billets or blooms whose thickness varies by about 70 to 110 mm.

The contact surface 26 of the head 1 is made from a highly wear-resistant sliding material and as shown in FIG. 1 is substantially planar for engagement with the substantially planar slab surface 10.

Each inspecting head 1 comprises two marking devices 24 which visibly mark the defects detected by the inspecting means 6 and the boundaries of the scanning strips on the slab surface.

Figures 3, 4, 5:
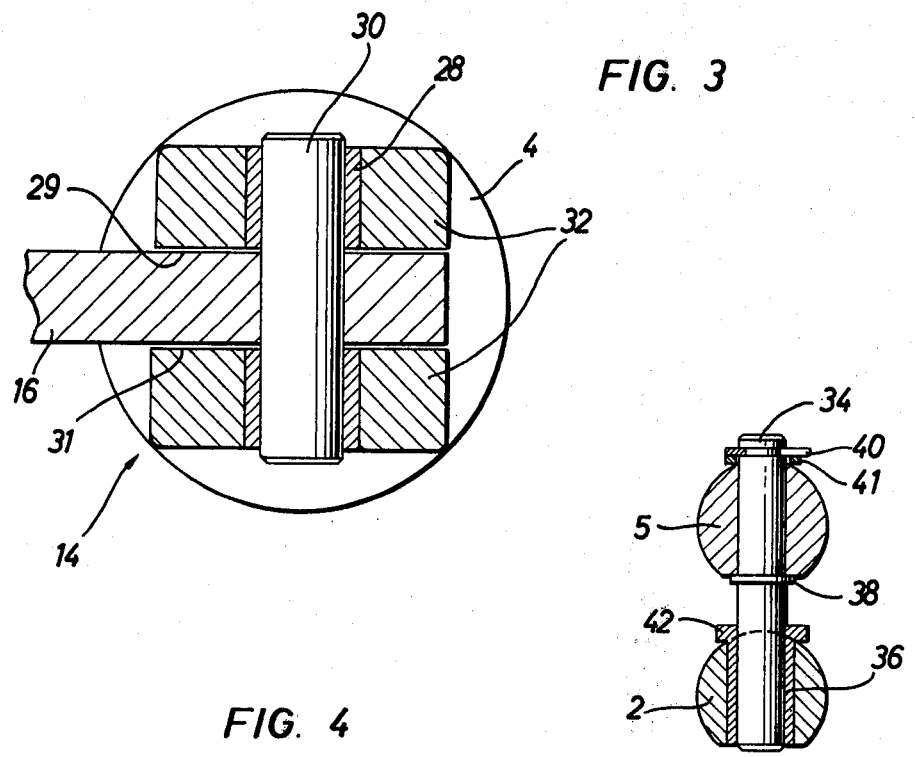
FIG. 3 is a partial section along the line III—III of FIG. 1 of a detail showing the mounting of the inspecting heads to an enlarged scale.
FIG. 4 is a partial plan view of a modified embodiment of the tension members transmitting the tension forces to the inspecting head, to an enlarged scale.
FIG. 5 is a section along the line V—V of FIG. 4.

FIG. 3 shows a partial section along the line III—III of FIG. 1 of an embodiment of the swivel joint 14 to an enlarged scale, said joint effecting the constrained guiding of the head 1 in the desired travelling direction 7. In the holder 16 a pivot pin 30 made preferably from steel is pressed firmly into a corresponding bore whose diameter is made somewhat smaller than the diameter of the pin in such a manner that the ends thereof projecting to equal extents on both sides of the holder 16 are rotatably mounted in corresponding bearing bushes 28 ofthe legs 32, which represent bearing plates and are fixedly connected to the pressure tie member 4, the bearing bushes 28 being disposed fixedly in the legs 32 and consisting of a conventional sliding bearing material.

The bearing bushes 28 and the pivot pin 30 are preferably shrunk into the legs 32 and the holder 16 respectively. The axial play between the inner bearing surfaces 31 of the legs 32 and the cooperating surfaces 29 of the holder 16 is just large enough as is necessary for a pivoting of the pressure tie member 4 about the pivot pin 30.

Each inspecting head comprises in the interior inspecting means 6 which are fixedly mounted in the region of the contact surface 26 or are reciprocal transversely of the travelling direction of the inspecting head. Preferably, the inspecting means 6 are probes measuring a magnetic stray or leakage field, in particular surface-wave probes, magnet-sensitive semiconductors, induction coils or the like, each head 1 comprising at least two such probes which are connected in differential circuit and the line joining which preferably extends perpendicularly to the scanning direction. Advantageously, two consecutive measurements are made for example to detect reliably elongated cracks independently of the travelling diection 7 of the inspecting heads 1. The two measurements are generally carried out at an angle of 90° to each other. This may advantageously be achieved with leakage flux techniques in that by means of a first magnetizing device not illustrated a magnetization at 45° to the travelling direction 7 is effected and the corresponding magnetic stray field measured by the probe pair and that a second magnetizing device which is not illustrated an is disposed behind the first produces a magnetization perpendicular to the first magnetization and the stray field thereof is also measured by the probe pair, the signals obtained on the basis of the two magnetizations being combined to determine the location of the defects and their maximum depth. The same effect can also be achieved by providing in each inspecting head at least three inspecting means whose connecting lines lie at an angle of preferably 45° to 135° to the longitudinal direction and whose inclination is in each case reversible so that firstly a defect inspection is possible at an angle of 45° to the travelling direction and secondly an inspection at an angle of 135° to the travelling direction.

According to the invention the inspecting means 6 may also be eddy current probes, in particular for defect detection in metallic but non-magnetizable bodies, each inspecting head 1 comprising at least one eddy current probe whose scanning width is equal to the distance between two receiving devices of said probe which respond to the field which is reflected back from the slab by the eddy currents at two separate locations in said slab, the receiver devices effecting the production of a differential signal which corresponds to the difference between the eddy current at said locations.

FIG. 4 shows a partial plan view of a modified embodiment of the tension members 2 and 5 transmitting the tension forces to the head 1 to an enlarged scale, a substantially cylindrically formed connecting pin 34 being passed through the tension members at the intersection of said crossed members 2 and 5 in the direction perpendicular to the plane formed by the two tension members in the untwisted position, said pin being non-displaceable in the upper member 5 in the direction of its axis but displaceably mounted in the lower member 2 in the direction of its axis so that an alteration of the angle formed by the tension members 2 and 5 is prevented even in the case of mutual twisting thereof and thus a lateral deviation of the inspecting heads 1 connected to the tension members 2 and 5 via the ball head joints 20 out of the travelling direction 7 is avoided.

FIG. 5 shows in section along the line V—V of FIG. 4 a mounting of the connecting pin 34 in the tension members 2 and 5 to an enlarged scale. The connecting pin 34 comprises in its upper half an annular shoulder 38 on which the lower side of the upper tension member 5 is held in engagement and which serves as stop preventing an axial displacement of the connecting pin 34 upwardly with respect to the tension member 5, a Seeger circlip ring 40 being provided to prevent axial displacement of the connecting pin 34 with respect to the tension member 5 downwardly. Between the Seeger ring 40 and the top of the upper tension member 5 is a compensating washer 41.

The connecting pin 34 is arranged displaceably in the direction of its axis with respect to the tension member 2 extending beneath the tension member 5, the member 2 comprising a bearing bush 36 in which the connecting pin 34 is slidingly mounted. The bearing bush 36 is fixedly connected to the member 2, preferably by shrinkage, and consists of a known sliding bearing material. The bush 36 comprises at its end face facing the upper tension member 5 an annular shoulder 42 which projects beyond the outer periphery of the bush 36 and which on mutual twisting of the tension members 2 and 5 serves as stop for the annular shoulder 38 of the connecting pin 34 and limits the mutual twisting of the members 2 and 5 in the clockwise sense seen in the travelling direction.

Figure 6:
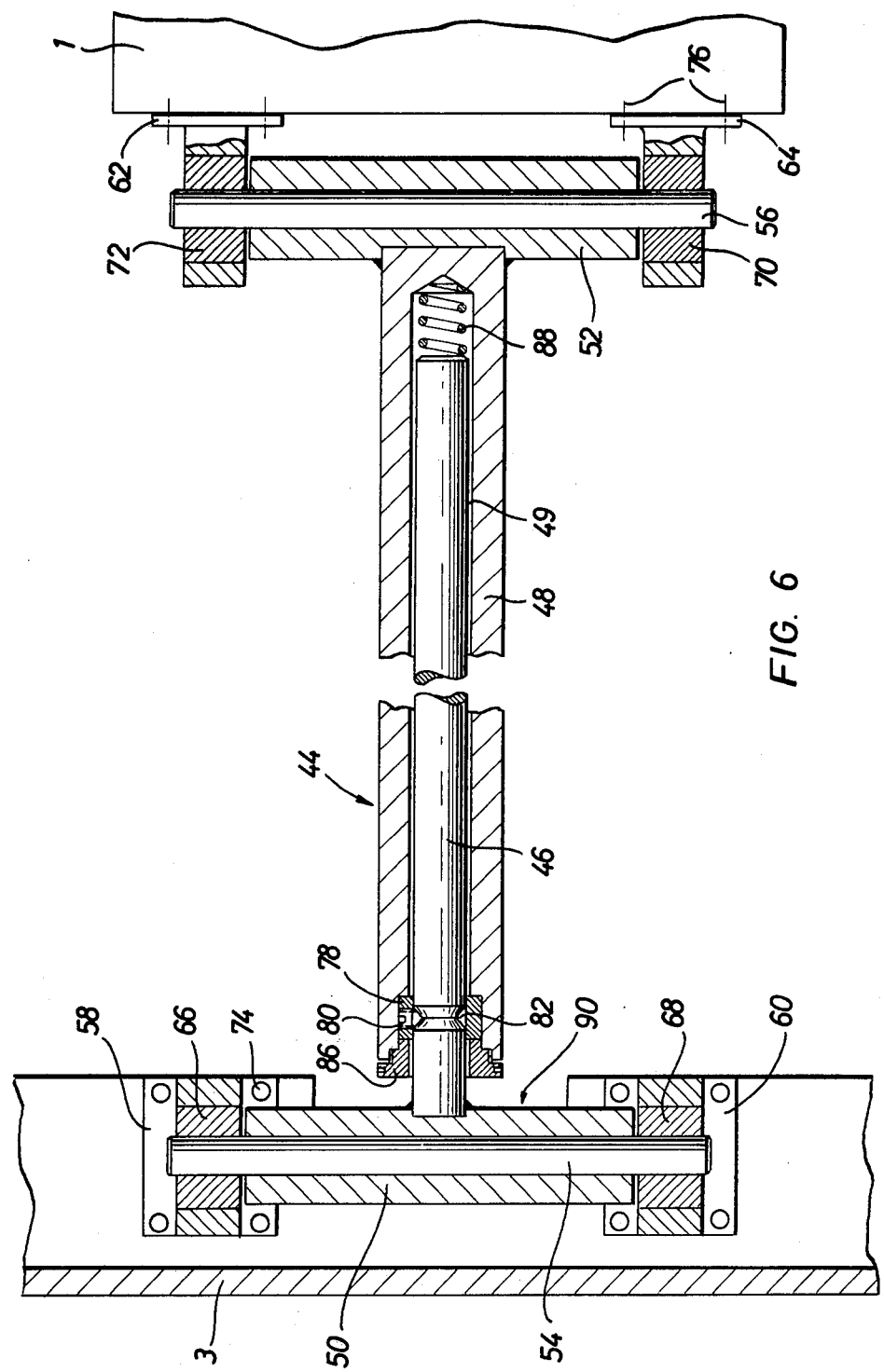
FIG. 6 is a further embodiment of the tension member shown in section.

FIG. 6 shows a further embodiment of the tension members in section, a single drawbar-like tie member 44 serving as tension member and consisting of two components rotatable relatively to each other about the longitudinal axis of the tie member 44, a cylindrically constructed guide rod 46 and a guide tube 48, the arrangement being such that the effective length of the tie members on turning the components 46 and 48 remains constant. The guide rod 46 is rotatably mounted in a bore 49 extending substantially through the entire component 48 and is substantially not displaceable axially.

Disposed on the guide rod 46 is a ring 78 which is connected to the guide rod 46 at least axially nondisplaceably preferably by means of grub screws 80 which are distributed at regular intervals over the periphery of the ring 78 and which in the screwed-in state cooperate positively with a wedge-shaped groove 82 extending over the periphery of the guide rod 46. The ring 78 is rotatable both by the tension force which is transmitted by the translatory movement in the travelling direction 7 of the support arm 3 to the inspecting head 1 and by a pressure spring 88 which is disposed between the end of the guide rod 46 and the axial bore 49 of the guide tube 48, but is held without axial play constantly in engagement with a closure cover 86 screwed into the guide tube 48. In this manner a pulling apart of the guide rod 46 and the guide tube 48 or a change of effective length of the member 44 is avoided when a tension force is applied to the head 1 with simultaneous mutual twisting of the guide tube 48 and the guide rod 46.

The guide rod 46 is fixedly connected to a sleeve 50, preferably welded, which is preferably shrunk onto a spindle 54 extending parallel to the slab surface 10 and transversely of the travelling direction 7, the spindle 54 being mounted with its ends rotatably in bearings 58 and 60. The bearings 58 and 60 are fixedly connected to the support arm 3 by means of screws 74. In this manner a pivoting of the member 44 is possible in a plane perpendicular to the spindle 54. The bearings 58 and 60 preferably comprise bearing bushes 66 and 68 which consist of a known sliding bearing material. The bush 50 extends substantially over the entire length of the spindle 54 until it bears with its preferably face-worked end faces on the inner opposing likewise face-worked end faces of the bearings 58 and 60 or bushes 66 and 68 in such a manner that a lateral displacement of the member 44 in the direction of the spindle 54 or perpendicularly to the travelling direction is substantially prevented.

To obtain a greater pivot range of the member 44, the lower edge of the support arm 3 between the bearings 58 and 60 comprises at the side facing the member 44 a recess 90 whose width corresponds at least to the maximum diameter of the member 44.

The guide tube 48 is fixedly connected in a similar manner to the guide rod 46 to a bush 52 which is preferably shrunk onto a spindle 56 extending substantially horizontally and transversely of the scanning direction, the spindle 56 being mounted with its end rotatably in bearings 62 and 64. The bearings 62 and 64 are connected by means of screws 76 fixedly to the rear wall of the inspecting head 1. In this manner, a pivoting between the member 44 and the head 1 about the spindle 56 is possible. The bearings 62 and 64 preferably comprise bearing bushes 70 and 72 which consist of a known sliding bearing material. The bush 62 extends substantially over the entire length of the spindle 56 until it bears with its preferably face-worked end faces on the inner opposing likewise face-worked end faces of the bearings 62 and 64 or bushes 70 and 72 in such a manner that a lateral displacement of the member 44 or the inspecting head 1 in the direction of the spindle 56 or perpendicular to the travelling direction 7 is substantially avoided.

The spacing of the bearings 58 and 60 or 62 and 64 respectively corresponds preferably approximately to the width of the inspecting heads 1. This achieves a maximum directional stability for the heads 1 drawn by the support arm 3 over the slab surface 10. The construction of the member 44 described above thus permits as does the crosswise arrangement of the members 2 and 5 a twisting of the member 44 with simultaneous superposition of a pivot movement of the tension members about the axis extending perpendicularly to the travelling direction 7 and parallel to the slab surface 10.

Since the weight of the inspecting head 1 and the resultant contact pressure at the slab surface 10 can be very high, to reduce the sliding friction the pressure member 4 constructed as piston and cylinder unit may be influenced in the stroke direction in such a manner that a part of the weight of the head is compensated and the inspecting head is held with a predetermined pressure force in engagement with the slab surface 10, said force being smaller than the weight of the head, preferably half said weight. Counterweights which are not illustrated may also be used to compensate the weight of the head 1.

What is claimed is:
1. Apparatus for non-destructive testing of an object in the form of a metal blank, especially steel slabs, flat steel or billets for defects such as cracks, seams, cavities, bubbles or the like disposed at or near the surface of the test object, comprising inspecting means for detecting defects at or near the surface of the test object and being arranged in at least one inspection head movable in a traveling direction relative to the surface of the test object, said at least one inspecting head being supported by a support arm member and having a contact surface for contacting the surface of the test object to be scanned, first and second connecting means for connecting said at least one inspecting head to said support arm member, said first connecting means extending in a direction substantially perpendicular to the contact surface of said at least one inspecting head, said first connecting means transmitting to said inspecting head forces substantially perpendicular to said contact surface of said at least one inspecting head, and said second connecting means extending in a direction substantially parallel to said contact surface of said at least one inspecting head, said second connecting means transmitting forces to said at least one inspecting head substantially exclusively in the travel direction of said at least one inspecting head and substantially parallel to the surface of the object to be scanned and preventing lateral displacement of the inspecting head from the traveling direction.

2. Apparatus according to claim 1, wherein said first connecting means includes means for moving said at least one inspecting head toward and away from the surface of the object to be scanned.

3. Apparatus according to claim 2, wherein the surface to be scanned is a substantially planar surface and the contact surface of said at least one inspecting head is a planar surface, said first connecting means providing a predetermined force for biasing the planar contact surface of said at least one inspecting head against the planar surface to be scanned.

4. Apparatus according to claim 2, wherein said first connecting means includes one of a double acting pneumatic and hydraulic cylinder.

5. Apparatus according to claim 1, wherein said first connecting means includes a tilt connection member at each end thereof, one tilt connection member being connected to said support arm member and the other tilt connection member being connected to said inspecting head, each of said tilt connection members being tiltable about an least one tilt axis extending substantially transversely to the travel direction and substantially parallel to the contact surface.

6. Apparatus according to claim 5, wherein at least one of the connection members permits tilting of said inspecting head about an axis extending parallel to the travel direction.

7. Apparatus according to claim 1, wherein said second connecting means includes at least one member having one end connected to the support arm member and another end connected to a lower region of said inspecting head, said at least one connecting member extending in a direction substantially parallel to the surface of the object to be scanned and being arranged for pivoting movement at least about a tilt axis extending substantially parallel to the surface of the object to be scanned and transversely of the travel direction.

8. Apparatus according to claim 7, wherein said second connecting means includes two connecting members extending transversely of one another and in overlying relationship, each connecting member being connected to said support arm member and to said inspecting head by ball joint connections.

9. Apparatus according to claim 8, wherein at least one of said connecting members is provided in the region of the overlapping relation with the other of said connecting members with a U-shaped curved portion extending about the other connecting member.

10. Apparatus according to claim 1, wherein said second connecting means includes a tie member having a longitudinal axis extending between said support arm member and said inspecting head, said tie member including at least two components rotatable with respect to each other about the longitudinal axis of said tie member such that the effective length of said tie member remains substantially constant on rotation of said components.

11. Apparatus according to claim 1, wherein said first connecting means includes one of a double acting pneumatic and hydraulic cylinder connected to said support arm member by a swivel joint having a pivot axis extending perpendicularly to the travel direction and parallel to the surface of the object to be scanned and connected to said inspecting head by a universal joint.

12. Apparatus according to claim 7, wherein said second connecting means includes two connecting members extending transversely to one another in overlying relation, and a connecting pin extending through said connecting members in the region of the overlying relation thereof such that no lateral displacement of said inspecting head from the path of movement thereof is permitted in response to twisting movement of said connecting members about an axis extending parallel to the travel direction.

13. Apparatus according to claim 12, wherein said connecting pin extends through said connecting members perpendicularly to a plane formed by said connecting members in an untwisted position, said connecting pin being fixedly arranged in one of said connecting members and displaceable in the other of said connecting members.

14. Apparatus according to claim 1, wherein a plurality of inspecting heads are provided, said inspecting heads being individually mounted on said support arm member in a line adjacent one another, the spacing between adjacent inspecting heads being substantially equal to the sensing width provided by said inspecting means associated with said inspecting head or an integral multiple thereof.

15. Apparatus according to claim 1, wherein said support arm member extends perpendicularly to the travel direction substantially over the entire surface of the object to be scanned and further comprising coarse adjusting means for adjusting said support arm member in the range of 500 to 600 mm with respect to the support surface of the object to be scanned, the distance of the lower edge of said support arm member from the surface of the object to be scanned being in the range of 50 to 60 mm.

16. Apparatus according to claim 15, wherein the length of the support arm member extending in the travel direction is equal to a portion of the maximum extent of the surface area to be inspected in the travel direction.

17. Apparatus according to claim 1, wherein at least one of said first and second connecting means enable movement of said at least one inspecting head with respect to a first position thereof at least 30 to 50 mm upwardly and at least 40 to 60 mm downwardly without substantially changing the pressure applied to said contact surface.

18. Apparatus according to claim 1, wherein said contact surface of said at least one inspecting head consists of a substantially highly wear-resistant sliding material.

19. Apparatus according to claim 18, wherein means are provided for counterbalancing the weight of said inspecting head.

20. Apparatus according to claim 19, wherein said counterbalancing means includes a piston-cylinder unit means for controlling the stroke direction thereof to counterbalance a portion of the weight of said at least one inspecting head associated therewith.

21. Apparatus according to claim 1, wherein the surface of the object to be scanned is a substantially planar surface and said second connecting means extends in a direction substantially parallel to said planar surface, and means for mounting said second connecting means at said support arm member and said at least one inspecting head, said mounting means being provided at two spaced apart locations on said support arm memer and at two spaced apart locations on said at least one inspecting head, said mounting means on said support arm being rigidly connected with one another and said mounting means on said at least one inspecting head being rigidly connected with one another.

22. Apparatus for non-destructive testing of blanks having substantially planar surfaces, especially steel slabs, flat steel or billets for defects such as cracks, seams, cavities, bubbles or the like disposed at or near the surface of the blank comprising inspecting means for detecting defects and arranged in at least one inspecting head movable in a traveling direction relative to the surface of the blank, said at least one inspecting head being supported by a support arm member and being provided with a substantially planar contact surface facing towards the blank for contacting the surface of the blank to be scanned with an adjustable contact pressure, said at least one inspecting head being movable along the surface of the blank, said at least one inspecting head being articulated to said support arm by articulating means including at least one first connecting member of variable length extending in a direction substantially perpendicular to the contact surface of said inspecting head and at least one second connecting member of substantially constant length extending in a direction substantially parallel to the contact surface of said inspecting head, said articulating means permitting movement of said inspecting head substantially only in a plane extending in the traveling direction and perpendicularly to the contact surface of said inspecting head.

* * * * *